(12) United States Patent
Murakami et al.

(10) Patent No.: US 8,083,669 B2
(45) Date of Patent: Dec. 27, 2011

(54) MEDICAL DEVICE FOR MAINTAINING STATE OF TREATMENT PORTION

(75) Inventors: Kazushi Murakami, Hino (JP); Yoshio Onuki, Hachioji (JP); Takaaki Komiya, Akiruno (JP); Hiroaki Ichikawa, Hachioji (JP); Yasuhito Kura, Hachioji (JP); Kazuki Honda, Hachioji (JP); Takehiro Nishiie, Akishima (JP)

(73) Assignee: Olympus Medical Systems Corp., Tokyo (JP)

( * ) Notice: Subject to any disclaimer, the term of this patent is extended or adjusted under 35 U.S.C. 154(b) by 877 days.

(21) Appl. No.: 11/821,332

(22) Filed: Jun. 22, 2007

(65) Prior Publication Data

US 2008/0319260 A1    Dec. 25, 2008

(51) Int. Cl.
*A61B 1/00*    (2006.01)
(52) U.S. Cl. ........................................ 600/106; 600/104
(58) Field of Classification Search .................. 600/104, 600/106, 107, 114–118; 606/205–209; 227/175.1–182.1
See application file for complete search history.

(56) References Cited

U.S. PATENT DOCUMENTS

| | | | | |
|---|---|---|---|---|
| 5,518,164 | A * | 5/1996 | Hooven | 227/5 |
| 5,817,119 | A * | 10/1998 | Klieman et al. | 606/174 |
| 2004/0019254 | A1 * | 1/2004 | Belson et al. | 600/146 |
| 2004/0176683 | A1 * | 9/2004 | Whitin et al. | 600/424 |
| 2005/0250989 | A1 * | 11/2005 | Suzuki | 600/106 |
| 2007/0078301 | A1 | 4/2007 | Kura et al. | |
| 2008/0183037 | A1 | 7/2008 | Ichikawa et al. | |

FOREIGN PATENT DOCUMENTS

| | | |
|---|---|---|
| JP | 2005-334132 | 12/2005 |
| JP | 2006-068076 | 3/2006 |
| JP | 2006-255257 | 9/2006 |
| WO | WO 01/54567 A1 | 8/2001 |
| WO | WO 2007/011040 A1 | 1/2007 |

* cited by examiner

*Primary Examiner* — Matthew J Kasztejna
*Assistant Examiner* — Ryan Henderson
(74) *Attorney, Agent, or Firm* — Scully, Scott, Murphy & Presser, P.C.

(57) ABSTRACT

A medical device of the invention includes: a treatment instrument including a treatment portion which is used extended from a distal end of an endoscope insertion portion having a treatment instrument channel, an operation portion for operation of advancing/retreating an operation wire coupled to the treatment portion, and a treatment instrument insertion portion in which the operation wire is advanceably/retreatably inserted, the treatment instrument insertion portion having a predetermined flexibility and inserted into the treatment instrument channel; a detecting portion for detecting advancing/retreating moving amount of the treatment instrument insertion portion; a treatment portion operating device to which the operation portion is installed, the treatment portion operating device advancing/retreating the operation wire to operate the treatment portion; an operation instructing portion for instructing operation of the treatment portion; and a control device for judging a state of the treatment instrument insertion portion and driving the treatment portion operating device by a moving amount obtained by correcting an advancing/retreating amount of the operation wire, based on a detection result from the detecting portion according to an instruction from the operation instructing portion.

11 Claims, 11 Drawing Sheets

FIG.5

| SHEATH MOVING AMOUNT | OPERATION WIRE CORRECTION AMOUNT |
|---|---|
| $L_0$ | $\ell_0$ |
| · | · |
| · | · |
| · | · |
| · | · |
| · | · |
| · | · |
| · | · |
| · | · |
| · | · |
| · | · |
| · | · |
| $L_{n-1}$ | $\ell_{n-1}$ |
| $L_n$ | $\ell_n$ |

FIG.10

| SHEATH MOVING AMOUNT | OPERATION WIRE CORRECTION AMOUNT | |
|---|---|---|
| | OPENED TREATMENT PORTION | CLOSED TREATMENT PORTION |
| $L_0$ | $w1_0$ | $w2_0$ |
| · | · | · |
| · | · | · |
| · | · | · |
| · | · | · |
| · | · | · |
| · | · | · |
| · | · | · |
| · | · | · |
| · | · | · |
| · | · | · |
| · | · | · |
| $L_{n-1}$ | $w1_{n-1}$ | $w2_{n-1}$ |
| $L_n$ | $w1_n$ | $w2_n$ |

MEDICAL DEVICE FOR MAINTAINING STATE OF TREATMENT PORTION

BACKGROUND OF THE INVENTION

1. Field of the Invention

The present invention relates to a medical device including a treatment instrument for performing a treatment to biological tissues, and in particular, to a medical device including an endoscope to be inserted into a body cavity and various treatment instruments to be used along with the endoscope.

2. Description of Related Art

As is well-known, endoscopes are widely used in the industrial or medical field. An endoscope as a medical device that is used in the medical field has an insertion portion to be inserted into a body cavity of the subject to perform an observation. With this endoscope, various treatments can be performed by leading a treatment instrument into the body cavity through a treatment instrument channel provided in the insertion portion.

When performing a treatment to body cavity tissues using the treatment instrument, an operator leads the treatment instrument into the body cavity through the treatment instrument channel of the endoscope. In doing so, the operator grasps an operation portion of the endoscope with one hand. Therefore, when inserting the treatment instrument into the treatment instrument channel, the operator holds a sheath which is an insertion portion of the treatment instrument with the other hand, to insert the sheath into the treatment instrument channel by manual operation. At this time, proximal end side of the sheath is grasped by staff such as nurses. This is to prevent a part of the sheath that reaches as much as, for example, 2 meters from contacting the floor or the like, which is an unclean area, during the insertion operation.

On the other hand, for example, when extracting body tissues using the treatment instrument, the operator grasps the operation portion of the endoscope with one hand. Therefore, it is impossible for the operator to hold the insertion portion of the endoscope and operate the operation portion of the treatment instrument with the other hand. Accordingly, the endoscope insertion portion is held, or the treatment instrument operation portion is operated by the staff. In other words, when inserting the sheath of the treatment instrument into the treatment instrument channel of the endoscope and when operating the treatment instrument, staff assistance was necessary.

Incidentally, in recent years, developments have been progressed for treatment instruments for endoscope not requiring such staff assistance. Japanese Unexamined Patent Publication Nos. 2006-68076 and 2006-255257, for example, disclose endoscope treatment instruments including a housing device in which a sheath can be wound and housed.

These conventional endoscope treatment instruments are disclosed to be designed with techniques to pull and relax an operation wire for operating a treatment portion in a constant operation stroke according to change of shape of the sheath, and to prevent the winding of the sheath from causing resistance force that disturbs advancing/retreating of the operation wire.

SUMMARY OF THE INVENTION

A first medical device of the present invention includes: a treatment instrument including a treatment portion which is used extended from a distal end of an endoscope insertion portion having a treatment instrument channel, an operation portion for operation of advancing/retreating an operation wire coupled to the treatment portion, and a treatment instrument insertion portion in which the operation wire is advanceably/retreatably inserted, the treatment instrument insertion portion having a predetermined flexibility and inserted into the treatment instrument channel; a detecting portion for detecting advancing/retreating moving amount of the treatment instrument insertion portion; a treatment portion operating device to which the operation portion is installed, the treatment portion operating device advancing/retreating the operation wire to operate the treatment portion; an operation instructing portion for instructing operation of the treatment portion; and a control device for judging a state of the treatment instrument insertion portion and driving the treatment portion operating device by a moving amount obtained by correcting an advancing/retreating amount of the operation wire, based on a detection result from the detecting portion according to an instruction from the operation instructing portion.

A second medical device of the present invention includes an endoscope including an endoscope insertion portion having a treatment instrument channel; a treatment instrument including a treatment portion which is used extended from a distal end of the endoscope insertion portion, an operation portion for operation of advancing/retreating an operation wire coupled to the treatment portion, and a treatment instrument insertion portion in which the operation wire is advanceably/retreatably inserted, the treatment instrument insertion portion having a predetermined flexibility and inserted into the treatment instrument channel; a detecting portion for detecting advancing/retreating moving amount of the treatment instrument insertion portion; a treatment portion operating device to which the operation portion is installed, the treatment portion operating device advancing/retreating the operation wire to operate the treatment portion; an operation instructing portion for instructing operation of the treatment portion; and a control device for judging a state of the treatment instrument insertion portion and driving the treatment portion operating device by a moving amount obtained by correcting an advancing/retreating amount of the operation wire, based on a detection result from the detecting portion according to an instruction from the operation instructing portion.

The above and other objects, features and advantages of the invention will become more clearly understood from the following description referring to the accompanying drawings.

BRIEF DESCRIPTION OF THE DRAWINGS

FIG. 5 is a view showing a control table of a correction moving amounts of position of a slider for pulling and relaxing an operation wire, corresponding to moving amounts of the sheath according to the first embodiment.

FIG. 10 is a view showing a control table of correction moving amounts of position of a slider for pulling and relaxing an operation wire, corresponding to moving amounts of the sheath, when performing opening/closing operation of the treatment portion according to the second embodiment.

DETAILED DESCRIPTION OF PREFERRED EMBODIMENTS

Figure 1:
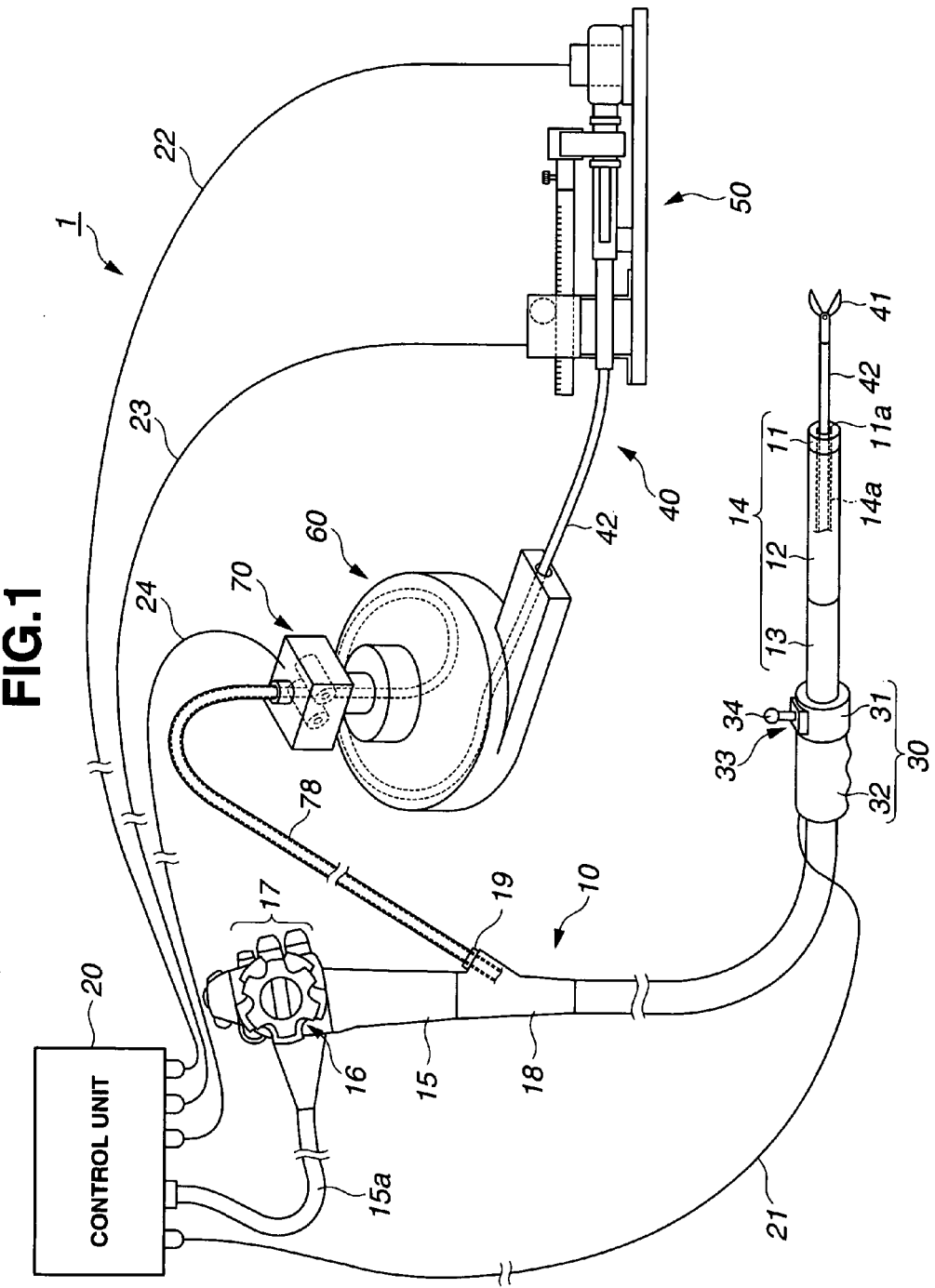
FIG. 1 is a view showing a configuration of an endoscope system according to a first embodiment.

Referring to the drawings, embodiments of the present invention are described below.

First Embodiment

First, a first embodiment of the present invention is described below using FIGS. 1 to 7.

Figure 2:
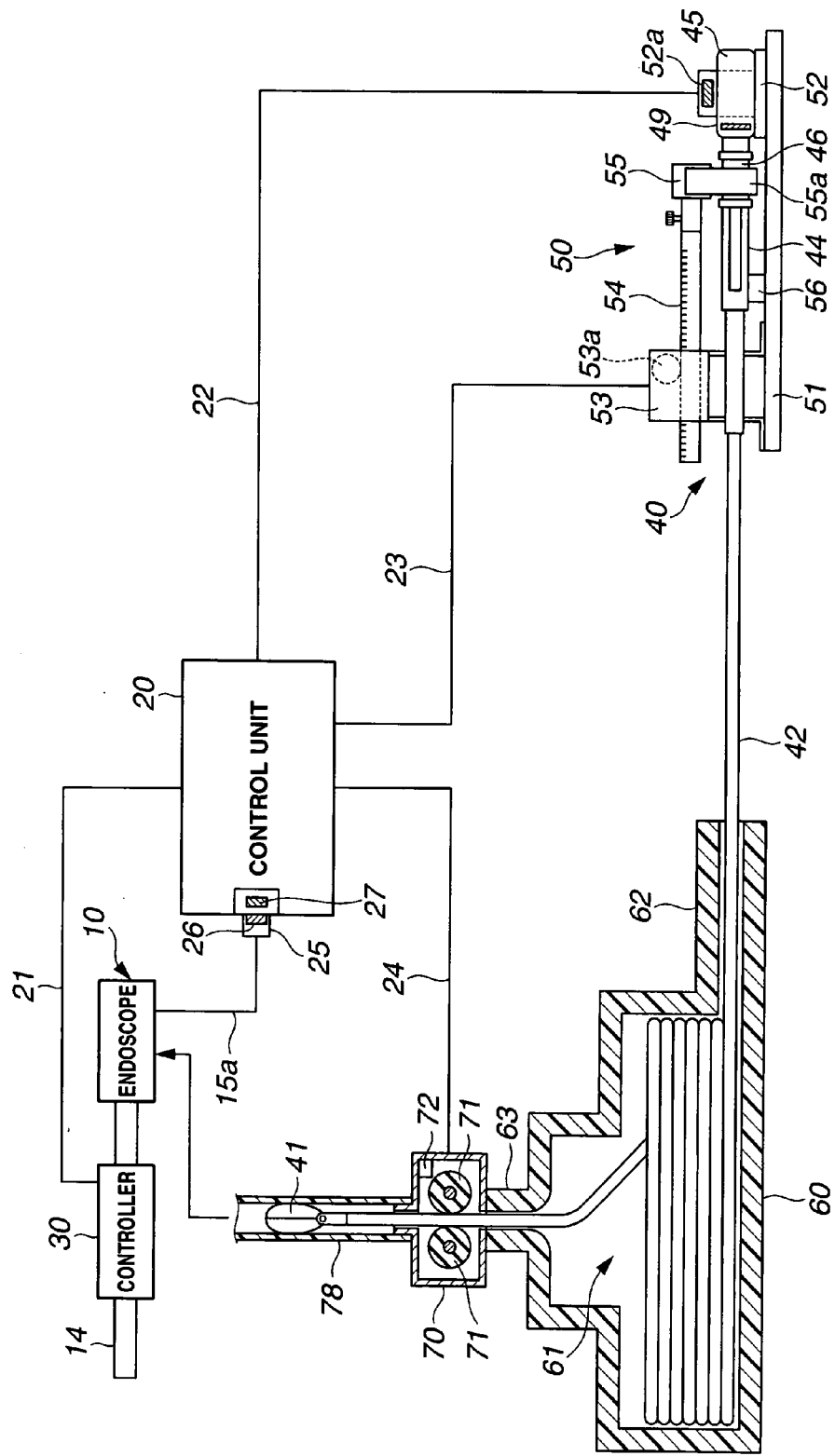
FIG. 2 is a view including a block diagram showing the configuration of the endoscope system of FIG. 1 according to the first embodiment.
Figure 3:
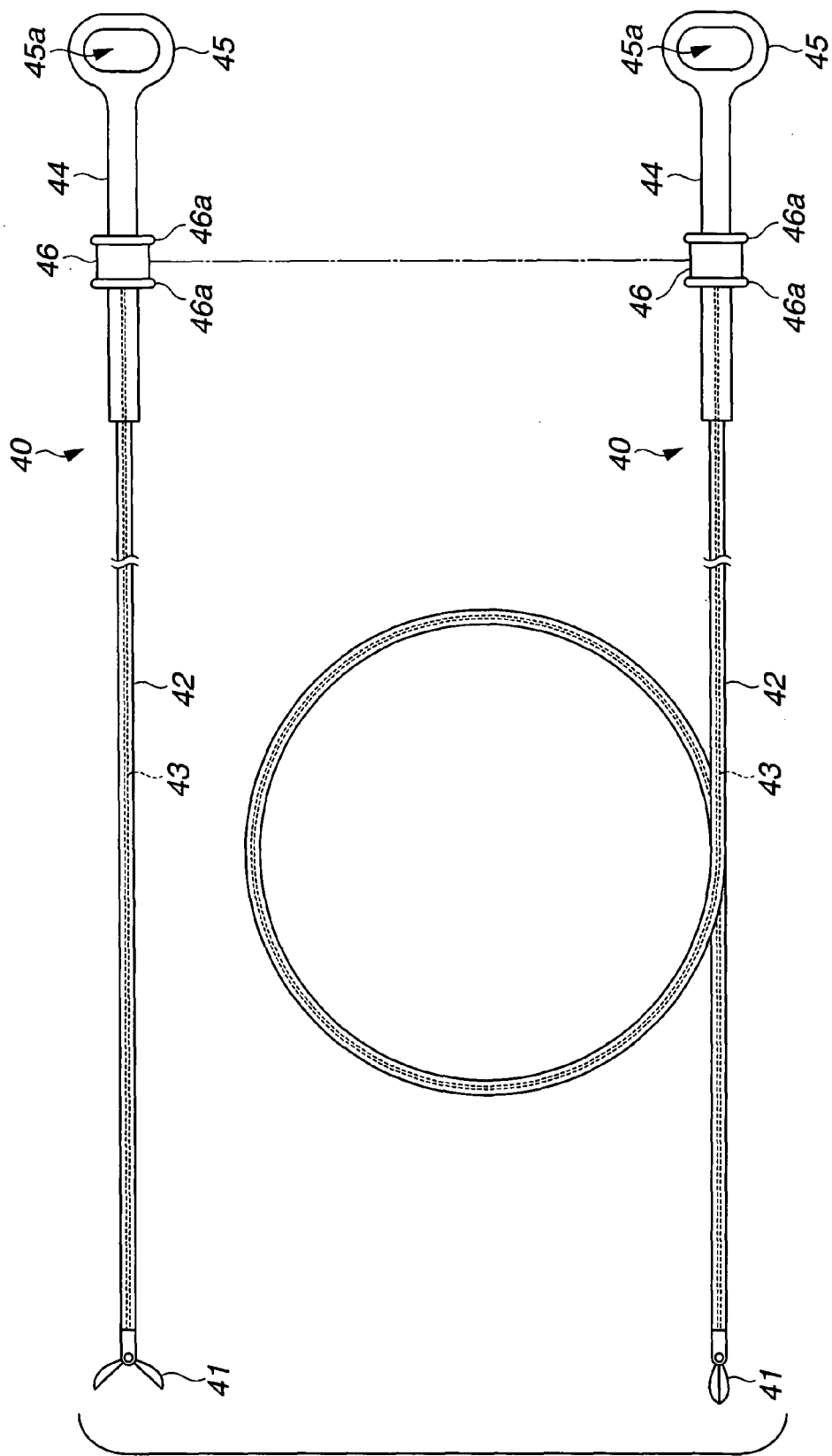
FIG. 3 is a plan view showing configurations of the same two treatment instruments according to the first embodiment and showing states of a treatment portion due to characteristics of a sheath which is a coil-type sheath.
Figure 4:
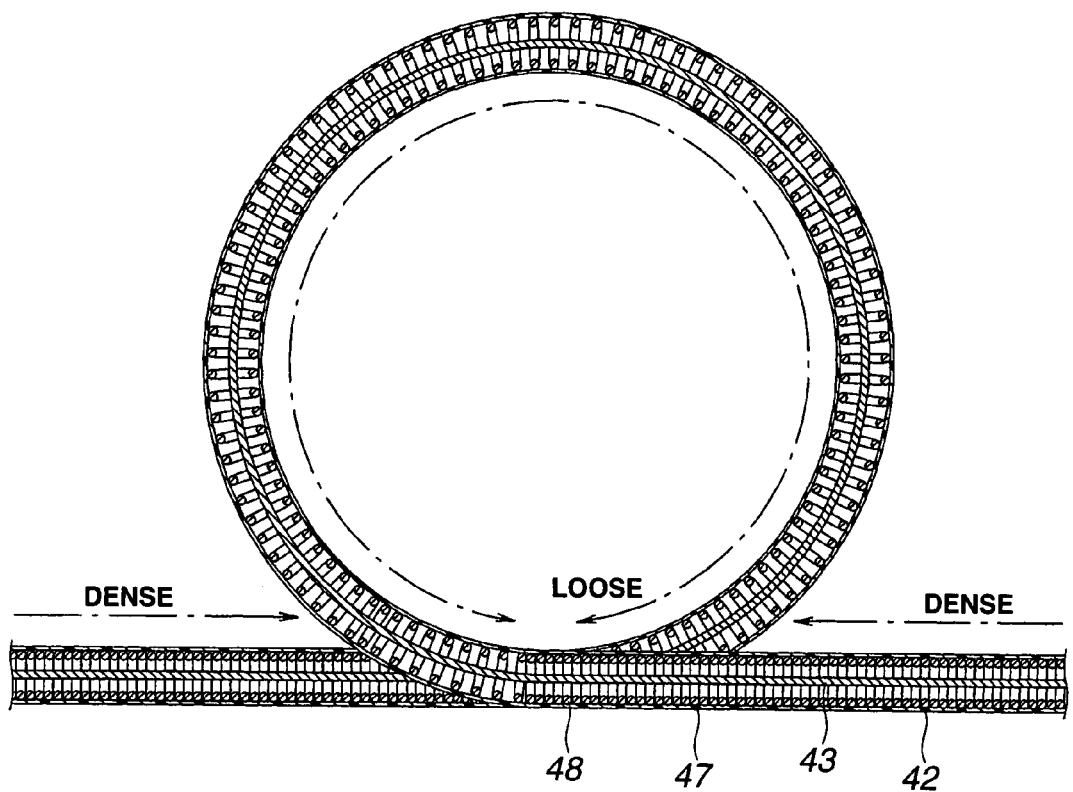
FIG. 4 is a section view showing the inside of the coil sheath in a looped state of the treatment instrument according to the first embodiment.
Figure 6:
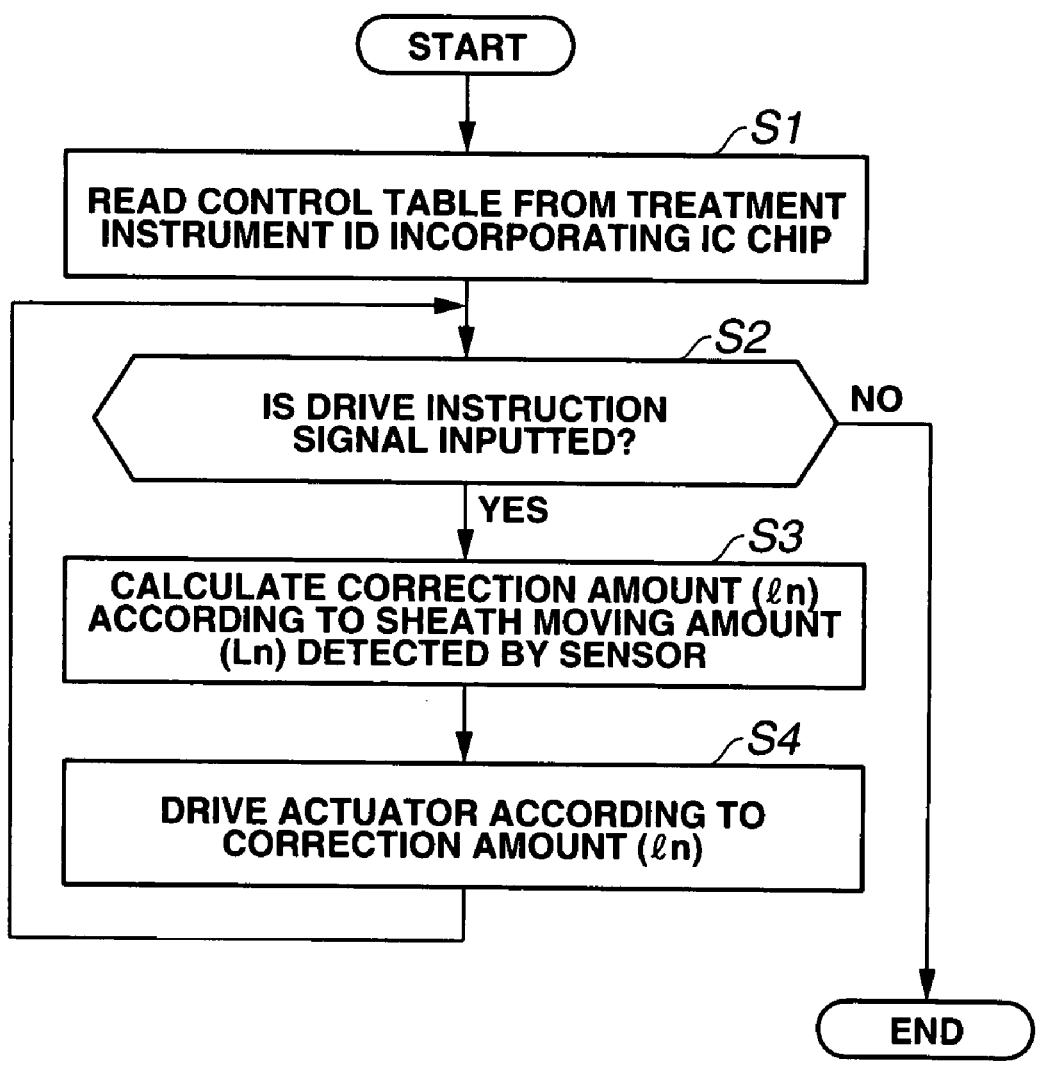
FIG. 6 is a flow chart of a control performed by a control device according to the first embodiment.
Figure 7:
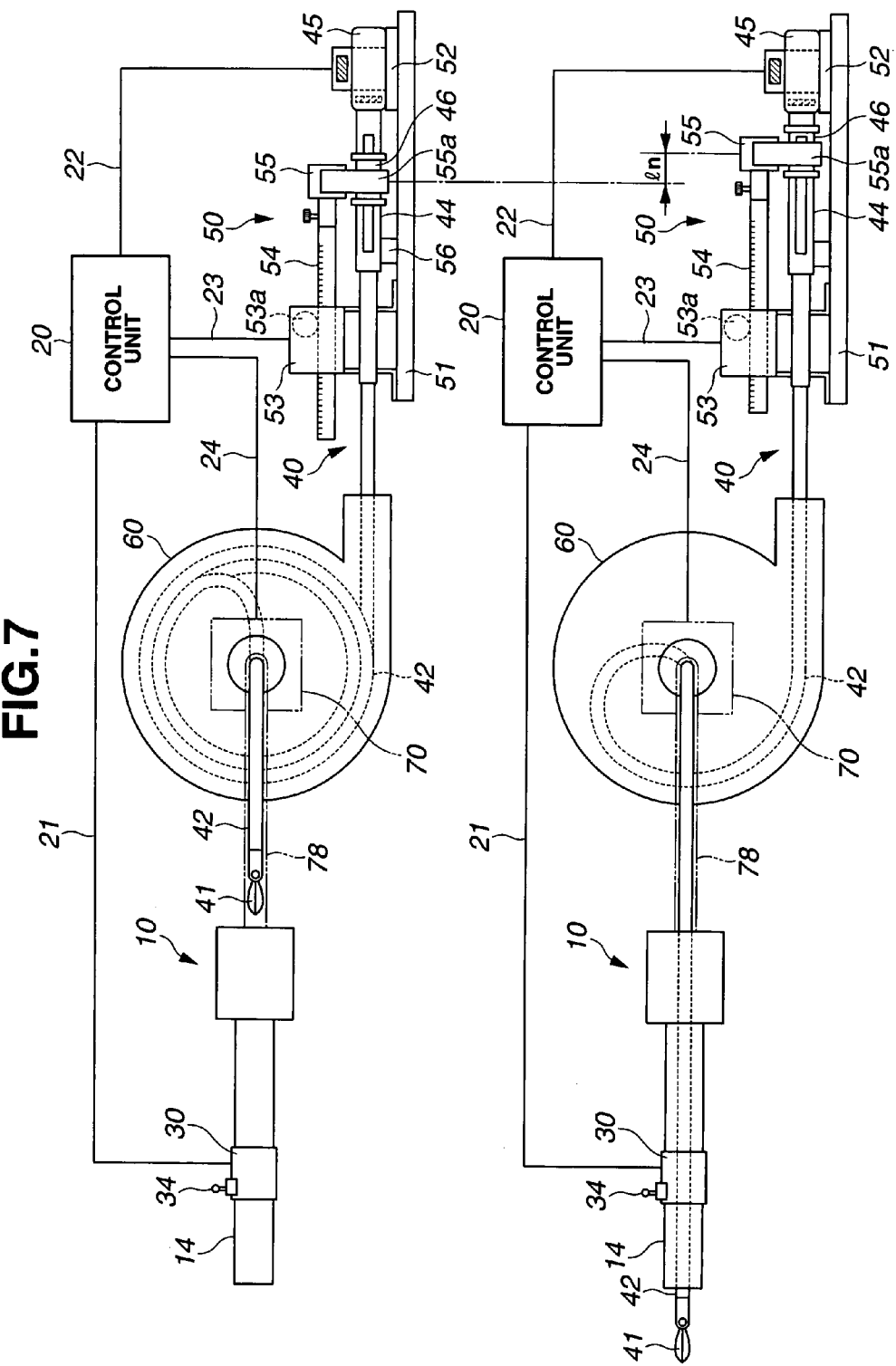
FIG. 7 is a view to illustrate states of the treatment portion of the treatment instrument accompanying the control of the endoscope system according to the first embodiment.

Note that, FIGS. 1 to 7 relate to the first embodiment of the present invention, where FIG. 1 is a view showing a configuration of an endoscope system; FIG. 2 is a view including a block diagram of the configuration of the endoscope system of FIG. 1; FIG. 3 is a plan view showing configurations of the same two treatment instruments and showing states of a treatment portion corresponding to states of a coil sheath; FIG. 4 is a section view showing the inside of the coil sheath in a looped state of the treatment instrument; FIG. 5 is a view showing a control table of correction moving amounts of the position of a slider for pulling and relaxing an operation wire, corresponding to moving amounts of the sheath; FIG. 6 is a flow chart of a control performed by a control device; and FIG. 7 is a view to illustrate states of the treatment portion of the treatment instrument involved in the control of the endoscope system.

As shown in FIG. 1, an endoscope system 1 which is a medical device of the present embodiment mainly includes an endoscope 10; a control device 20 serving both as a light source device and a video processor; a controller 30 serving as an operation instructing device; a treatment instrument 40 including a treatment portion 41 for performing a predetermined treatment to body cavity tissues; a treatment instrument electrical drive operating device 50 serving as a treatment portion operating device for operating the treatment portion 41 by electrical drive; a housing case (hereinafter referred to as a case body) 60 in which a sheath 42 as a treatment instrument insertion portion of the treatment instrument 40 is wound and housed; and a treatment instrument insertion portion electrical drive advancing/retreating device (hereinafter referred to simply as an electrical drive advancing/retreating device) 70 serving as a treatment instrument advancing/retreating device for advancing and retreating the sheath 42 of the treatment instrument 40.

The endoscope 10 shown in FIG. 1 is configured by an endoscope insertion portion (hereinafter abbreviated as an insertion portion) 14 including a distal end portion 11, a bending portion 12, and a flexible tube portion 13, these being provided in a linked manner; an operation portion 15 connected with the insertion portion 14; and a universal cord 15a that is detachably connected to the control device 20.

The operation portion 15 of the endoscope 10 serves also as a grasping portion for an operator, and is provided on a proximal end side of the insertion portion 14. The universal cord 15a extends from a side portion of the operation portion 15, and has at a proximal end a connector portion that is detachably connected to the control device 20.

The insertion portion 14 of the endoscope 10 is configured by, in the following order from a distal end side, the rigid distal end portion 11, the bending portion 12 which is bendable, and the flexible tube portion 13 having flexibility, these being provided in a linked manner. The distal end portion 11 is provided with a distal end aperture 11a.

The operation portion 15 of the endoscope 10 is provided with a bend preventing portion 18 connected with a proximal end of the flexible tube portion 13. The operation portion 15 is equipped with two bending knobs 16 for bending operation of the bending portion 12, function switches 17 including an air/water feeding button for feeding air and water and a suction button for performing suction, various switches for controlling an endoscope image obtained by image pickup devices provided in the distal end portion 11, and the like.

Note that the insertion portion 14 of the endoscope 10 is disposed with a treatment instrument channel 14a having an aperture at a treatment instrument insertion port 19 provided to the bend preventing portion 18 and communicating with the distal end aperture 11a.

The controller 30 shown in FIG. 1 has a generally cylindrical shape to allow slidable external insertion and placement on the insertion portion 14 of the endoscope 10. The controller 30 is configured by a rigid main body portion 31, and a grip body 32 which is, for example, an elastic member provided in a linked manner to the main body portion 31. From a proximal end surface side of the grip body 32, a signal cable 21 is extended. A proximal end side of the signal cable 21 is detachably electrically connected to the control device 20.

On a circumferential side surface of the main body portion 31, an operation instructing portion 33 is provided. The operation instructing portion 33 has an operation lever 34 of joystick type, for example. By the operator operating to incline the operation lever 34 toward a distal end side, an instruction signal for advancing the sheath 42 of the treatment instrument 40, to be described later, is outputted from the operation instructing portion 33 to the control device 20. Also, by operating to incline the operation lever 34 toward a proximal end side, an instruction signal for retreating the sheath 42 of the treatment instrument 40, to be described later, is outputted from the operation instructing portion 33 to the control device 20.

The control device 20 shown in FIG. 1 is provided with a lamp (not shown) to supply illumination light, a signal processing circuit (not shown), and the like. The signal processing circuit performs a processing for generating a drive signal for driving an image pickup device (not shown) such as CCD provided in the distal end portion of the endoscope, a processing for generating a video signal from an electrical signal transmitted from the image pickup device, and the like. The control device 20 is connected with a display device such as a liquid crystal display (not shown) to display an endoscope image.

In the present embodiment, the treatment instrument 40 shown in FIG. 1 is, for example, a biopsy forceps (hereinafter in the present embodiment described as a biopsy forceps 40) and includes the sheath 42 mentioned above which is a flexible tubular body having a predetermined elasticity.

The sheath 42 has, at a distal end part thereof, the treatment portion 41 configuring an opening/closing member which here is a tissue extracting portion. In the present embodiment, the treatment portion 41 as the tissue extracting portion is openably and closably configured by a pair of biopsy cups. In the sheath 42 of the biopsy forceps 40, an operation wire 43 (see FIG. 3) is inserted. The operation wire 43 is moved to advance and retreat through operation of a handle portion 44.

The handle portion 44 includes a finger-hook ring 45 and a slider 46. The finger-hook ring 45 has a hole portion 45a in which, for example, the thumb of a user is placed. The slider 46 is provided with a pair of flanges 46a on which the middle and third fingers of the user are placed.

In other words, the treatment portion 41 is changed from an opened state to a closed state or in an opposite manner by the operation wire 43 pulled and relaxed along with advancing/retreating operation of the slider 46 of the handle portion 44.

The case body 60 shown in FIG. 1 is a housing case having a hollow generally columnar shape in which to wind and house the sheath 42 of the biopsy forceps 40. The case body 60 includes a sheath housing portion 61 for housing the sheath 42 of the biopsy forceps 40, the sheath housing portion 61 providing a storage space for housing the sheath 42.

The case body 60 includes two sheath insertion portions communicating with the sheath housing portion 61. The two sheath insertion portion are respectively provided to a treatment instrument holding portion 62 having a block shape that is extendedly provided from a circumferential side surface, and to a sheath lead-out portion 63 projecting from a generally center of a top surface. That is, the two sheath insertion portions are placed to the case body 60 and communicate with the sheath housing portion 61 such that respective aperture portions face directions orthogonal to each other.

Note that, in the present embodiment, as for the biopsy forceps 40 wherein the sheath 42 is wound and housed in the case body 60, a halfway part on a proximal end side of the sheath 42 is fixed to the treatment instrument holding portion 62. Part of the sheath 42 on the distal end side than this fixed part is in a state freely inserted in the sheath lead-out portion 63.

The electrical drive advancing/retreating device 70 shown in FIG. 2 is detachably installed to the sheath lead-out portion 63 configuring the case body 60. The electrical drive advancing/retreating device 70 is electrically connected to the control device 20 by an electrical cable 24 in which a signal line is inserted. The electrical drive advancing/retreating device 70 has an action of advancing or retreating the sheath 42 of the biopsy forceps 40 based on operation of the operation lever 34 (see FIG. 1) of the controller 30.

The electrical drive advancing/retreating device 70 has inside an enclosure thereof two rotatable rollers 71. The two rollers 71 are each configured by an elastic resin member, one of the rollers being driven by a motor which is a driving source not shown.

In other words, the sheath 42 of the biopsy forceps 40 which is led in the enclosure of the electrical drive advancing/retreating device 70 is placed between the two rollers 71 via the sheath lead-out portion 63 of the case body 60. This causes an outer surface of the sheath 42 to be pressed and pinched by the two rollers 71.

The one of the rollers 71, which is rotated by the motor (not shown) as a driving source disposed in the electrical drive advancing/retreating device 70, advances/retreats the sheath 42 along a rotation direction, by means of friction by the pressing.

That is, by driving the motor in a state where the sheath 42 is pinched between the two rollers 71, the sheath 42 pinched between the two rollers 71 are moved along with rotation of the one of the rollers 71. In other words, the sheath 42 is advanced or retreated in the treatment instrument channel 14a of the endoscope 10 by controlling the rotation direction of the motor in the electrical drive advancing/retreating device 70.

The drive control of the motor of the electrical drive advancing/retreating device 70 is performed by the control device 20 based on operation of the operation lever 34 of the controller 30. Note that the rollers 71 are rotatably supported by a rotation shaft fixed to the enclosure or a motor shaft of the motor such that respective roller surfaces are apart from each other by a predetermined clearance.

Furthermore, the electrical drive advancing/retreating device 70 incorporates a rotation detecting sensor 72 which is a detecting portion for detecting the number of rotations of the rollers 71. A detection value of the rotation detecting sensor 72 is outputted to the control device 20 via the electrical cable 24. That is, the control unit 20 calculates a moving amount (extension amount) of the sheath 42 of the biopsy forceps 40 based on a detection value from the rotation detecting sensor 72. The sensor for detecting the moving amount (extension amount) of the sheath 42 of the biopsy forceps 40 is not limited to the rotation detecting sensor 72 for detecting the number of rotations of the rollers 71. For example, an optical sensor for counting indexes provided at equal intervals on the sheath 42 or reading coarseness (minute concavities and convexities) of the surface of the sheath 42 may also be used, and based on a detection result of the optical sensor, the control device 20 may calculate the moving amount (extension amount) of the sheath 42 of the biopsy forceps 40. Also, an encoder may be provided to the motor itself to directly detect the number of rotations.

Note that symbol 78 represents a coupling tube. One end portion of the coupling tube 78 is attached to the treatment instrument insertion port 19 of the endoscope 10, and the other end portion is attached to the electrical drive advancing/retreating device 70. Therefore, the sheath 42 of the biopsy forceps 40 which is led out to the outside of the case body 60 is led into the treatment instrument channel 14a via the coupling tube 78.

The electrical drive operating device 50 shown in FIGS. 1 and 2 includes a board-shaped base body 51. The base body 51 is provided with a ring retaining portion 52, a holding box 53, and a mounting portion 56.

The holding box 53 which is an actuator is fixed to the base body 51 through foot portions. In the holding box 53, a rack 54 forming straight teeth is held in a straightly advanceable/retreatable manner. In the holding box 53 is disposed a pinion gear 53a that engages with the straight teeth of the rack 54.

The pinion gear 53a is fixed to a motor shaft of a motor not shown. In other words, the motor is rotated in a state where the pinion gear 53a is engaged with the straight teeth provided to the rack 54. Then the pinion gear 53a fixed to the motor is rotated to move to advance/retreat the rack 54.

The holding box 53 is connected with one end of an electric cable 23 and the other end of the electric cable 23 is detachably electrically connected to the control device 20.

A slider retaining portion 55 including a holding portion 55a is attached to one end portion of the rack 54 by means of a screw. The holding portion 55a of the slider retaining portion 55 pinches the slider 46 provided to the handle portion 44 of the biopsy forceps 40. Specifically, the holding portion 55a holds the slider 46 in a manner pinching a trunk portion between a pair of flanges 46a provided to the slider 46.

Note that, in the present embodiment, driving instructions for the motor in the holding box 53 are performed by an operation of inclining the operation lever 34 of the controller 30 to right and left sides. As an example thereof, when the operation lever 34 is inclined to the right side with respect to the forward direction of the controller 30, the slider 46 is moved in a direction where the rack 54 pushes forward the operation wire 43 by means of the holding box 53. On the contrary, when the operation lever 34 is inclined to the left side with respect to the forward direction of the controller 30, the slider 46 is moved in a direction where the rack 54 pushes backward the operation wire 43 by means of the holding box 53.

In the ring retaining portion 52 is inserted and placed the hole portion 45a of the finger-hook ring 45 provided to the handle portion 44 of the biopsy forceps 40. This causes the handle portion 44 of the biopsy forceps 40 to be unitedly fixed to and held to the electrical drive operating device 50.

The ring retaining portion 52 is connected with one end of a communication cable 22 and the other end of the communication cable 22 is detachably electrically connected to the control device 20. Note that, the communication cable 22 may be a signal cable composite with the electric cable 23 connected to the above-mentioned holding box 53.

When the finger-hook ring 45 is inserted and placed in the ring retaining portion 52 in a predetermined state, a part of the handle portion 44 is placed on the mounting portion 56 of the base body 51. This causes the handle portion 44 of the biopsy forceps 40 to be placed parallel with the base body 51 in a state apart therefrom by a predetermined distance.

As shown in FIG. 2, the control device 20 of the present embodiment is provided with an endoscope ID reading sensor 27 which here is an RFID (Radio Frequency Identification) reading portion that reads endoscope information provided in the connector 25 when the connector 25 of the universal cord 15a of the endoscope 10 is connected to the control device 20.

The endoscope ID reading sensor 27 reads model type information of the endoscope 10 connected, length of the insertion portion 14, channel length of the treatment instrument channel 14a disposed in the insertion portion 14, and the like, from an endoscope ID incorporating IC chip 26 incorporated in the connector 25 of the universal cord 15a.

Moreover, the ring retaining portion 52 of the electrical drive operating device 50 is provided with a treatment instrument ID reading sensor 52a which here is an RFID (Radio Frequency Identification) reading portion that reads treatment instrument information when the finger-hook ring 45 is inserted and placed in the ring retaining portion 52 in a predetermined state.

The treatment instrument ID reading sensor 52a reads model type information of the biopsy forceps 40 disposed, length of the sheath 42, the number of windings of the sheath 42 in the initial state, inside diameter of the sheath housing portion 61 of the case body 60, and the like, from a treatment instrument ID incorporating IC chip 49 such as an integrated circuit which here is incorporated in the finger-hook ring 45 of the biopsy forceps 40. The model type information and the like here of the biopsy forceps 40 read by the treatment instrument ID reading sensor 52a is outputted to the control device 20 via the communication cable 22.

Here, based on FIGS. 3 and 4, described below are characteristics in the configuration of the biopsy forceps 40 used in the endoscope system 1 of the present embodiment.

The biopsy forceps 40 of the present embodiment has a configuration conventionally used, and is a coil sheath type (see FIG. 4) with a predetermined flexibility, including a coil tube 47 wherein the sheath 42 is made of a metallic wire of stainless or the like wound into a tube shape, and a flexible tube envelope 48 covering the coil tube 47. Note that the sheath 42 of the coil sheath type may be configured only of the coil tube 47 not including the tube envelope 48.

As for the biopsy forceps 40, when the sheath 42 is looped with a predetermined radius while fixing the position of the slider 46 in a state where the treatment portion 41 is opened, the treatment portion 41 is brought to a closed state, as shown in FIG. 3. This is a phenomenon that occurs when the sheath 42 is a coil sheath type as in the present embodiment. Note that a typical biopsy forceps 40 has a configuration in which the treatment portion 41 is closed when the slider 46 is moved toward the user, that is, toward the side of the finger-hook ring 45.

When the sheath 42 including the coil tube 47 as mentioned above is generally straight, the coil tube 47 is in a dense state, whereas when the sheath 42 is looped, the coil tube 47 is brought into a loose state, as shown in FIG. 4. In other words, when the sheath 42 is looped, the entire length thereof is extended depending on the size and the number of the loops than when the sheath 42 is straight.

Accompanying therewith, with the biopsy forceps 40 wherein the sheath 42 has the coil tube 47, even when the position of the slider 46 is fixed, that is, the slider 46 is not moved, the treatment portion 41 is opened or closed because the operation wire 43 is pulled and relaxed in line with an expansion/contraction amount of the coil tube 47 depending on the loops, as shown in FIG. 3.

For this reason, if the slider 46 is in a fixed state while the biopsy forceps 40 is being operated to be fed toward the treatment instrument channel 14a of the endoscope 10 from a state of being wound and housed in the case body 60, the treatment portion 41 is opened and caught in the treatment instrument channel 14a in which the treatment portion is inserted through, which damages the treatment instrument channel 14a. This results in a problem of requiring the operator to stop the endoscopy and treatment.

Accordingly, the endoscope system of the present embodiment is configured such that, when the biopsy forceps 40 of the coil sheath type is advanced or retreated, the control device 20 performs control to correct the position of the slider 46 of the biopsy forceps 40 so that the treatment portion 41 retains the opening/closing state at that time.

In detail, the treatment instrument ID incorporating IC chip 49 of the biopsy forceps 40 of the present embodiment shown in FIG. 2 stores a control table shown in FIG. 5 in which correction moving amounts 0 to ln for the operation wire 43 are set, so as not to render changeable the opening/closing state of the treatment portion 41, with respect to moving amounts $L_0$ to Ln of the sheath 42 fed into the treatment instrument channel 14a of the endoscope 10 from the initial state of the sheath 42 wound and housed in the case body 60.

When the finger-hook ring 45 of the biopsy forceps 40 is installed in a predetermined manner to the ring retaining portion 52 of the electrical drive operating device 50, the information of the control table is read by the treatment instrument ID reading sensor 52a of the ring retaining portion 52 and outputted to the control device 20.

Then, the control device 20 performs control in line with the routine of the flow chart shown in FIG. 6 based on the inputted control table. Specifically, the endoscope system 1 is first set to the state shown in FIG. 2.

First, when leading the biopsy forceps 40 into the treatment instrument channel 14a of the endoscope 10, the operator operates to incline forward the operation lever 34 of the controller 30. This causes the control device 20 to drive the electrical drive advancing/retreating device 70. Then, the sheath 42 of the biopsy forceps 40 is fed by the pinching two rollers 71 into the treatment instrument channel 14a of the endoscope 10 via the coupling tube 78.

At this time, the control device 20 performs control based on the routine (step S) of the flow chart shown in FIG. 6, triggered by an advancing/retreating drive instruction signal from the operation lever 34 of the controller 30.

First, the control device 20 reads the control table shown in FIG. 5 stored in the treatment instrument ID incorporating IC chip 49, inputted by the treatment instrument ID reading sensor 52a, as shown in FIG. 6 (S1).

Next, the control device 20 judges whether or not an advancing/retreating drive instruction signal is inputted from the operation lever 34 of the controller 30 (S2). Then, depending on a detection value of the rotation detecting sensor 72, the control device 20 calculates a moving amount Ln of the sheath 42 for this time and calculates a correction moving amount ln of the slider 46 corresponding to the moving amount Ln, from the control table shown in FIG. 5 read in step S1 (S3).

The control device 20 drives the holding box 53 serving as an actuator to move the slider 46 toward a predetermined direction by a correction moving amount ln thus calculated (S4). Here, because the sheath 42 of the biopsy forceps 40 is pulled out from the case body 60, the slider 46 is moved rearward by the correction moving amount ln.

Thereafter, the control device 20 returns to step S2 again to repeat the routine of these steps S2 to S4. Note that, if the advancing/retreating drive instruction signal is not inputted from the operation lever 34 of the controller 30 in step S3, the control device 20 ends the control flow chart of FIG. 6. That is, this is a state where the operator has not operated the operation lever 34 of the controller 30 and the advancing/retreating movement of the sheath 42 of the biopsy forceps 40 is stopped.

As described above, the control device 20 performs control so as not to render changeable the opening/closing state of the treatment portion 41 when the operation lever 34 of the controller 30 is activated, by correcting the position of the slider 46 that pulls and relaxes the operation wire 43 in line with the moving amount as a feeding amount of the sheath 42 of the biopsy forceps 40.

In other words, in the endoscope system 1 of the present embodiment, while the sheath 42 of the biopsy forceps 40 is being fed into the treatment instrument channel 14a of the endoscope 10, from the initial state of starting endoscopic operation and treatment to the state where the treatment portion 41 is protruded from the distal end portion 11 of the insertion portion 14 of the endoscope 10 as shown in FIG. 7, the sheath 42 can be moved with the treatment portion 41 constantly kept in a closed state.

Moreover, the endoscope system 1 controls the position correction of the slider 46 such that the opening/closing state of the treatment portion 41 is constantly maintained when the operation lever 34 of the controller 30 is activated, regardless of the advancing/retreating moving amount of the sheath 42.

As a result of the above, it is made possible to prevent the treatment portion 41 in a closed state from opening in the treatment instrument channel 14a of the endoscope 10, because the endoscope system 1 of the present embodiment performs control so as not to render changeable the opening/closing state of the treatment portion 41 when the sheath 42 of the biopsy forceps 40 wound and housed in the case body 60 is moved to be advanced/retreated.

Thus, the endoscope system 1 is configured to prevent the treatment portion 41 of the biopsy forceps 40 from being caught in the treatment instrument channel 14a, and the treatment instrument channel 14a from being damaged. Therefore, the endoscope system 1 can eliminate the problem of requiring the operator to stop endoscopy and treatment.

Further, in a state of pulling back the biopsy forceps 40, contrary to the above-mentioned feeding state thereof, if the biopsy forceps 40 extended from the distal end portion 11 of the endoscope 10 is moved in a retreat direction to be wound and housed in the case body 60 with the treatment portion 41 closed, without the above-mentioned control of the control device 20 being performed, then the internal operation wire 43 is further pulled. This results in a problem that the sheath 42 is stiffened, i.e., tensioned, thus disallowing the sheath 42 to be wound and housed in the case body 60.

However, in the endoscope system 1 of the present embodiment, by performing the above-mentioned control based on the flow chart of FIG. 6, the tension of the operation wire 43 for maintaining the opening/closing state of the treatment portion 41 is kept in a constant state, by means of the correction moving amount ln of the slider 46 that corresponds to the feeding amount (moving amount Ln) of the sheath 42. Therefore, the flexibility of the sheath 42 of the biopsy forceps 40 is kept constant and smoothly wound and housed in the sheath housing portion 61 of the case body 60 with the treatment portion 41 closed.

Second Embodiment

Next, a second embodiment of the present invention is described below using FIGS. 8 to 11.

Figure 8:
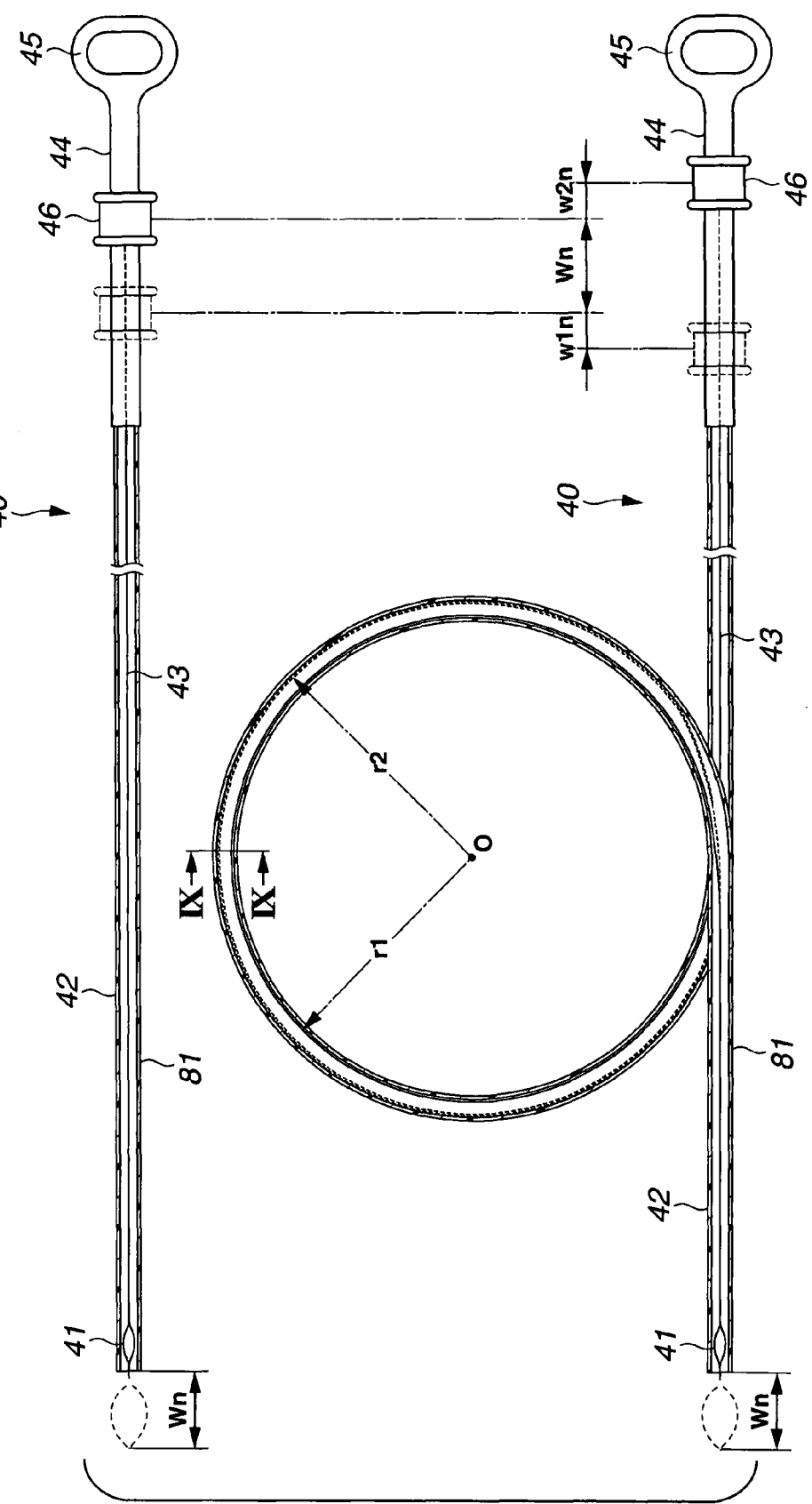
FIG. 8 is a plan view showing configurations of the same two treatment instruments according to a second embodiment and showing states of a treatment portion due to characteristics of the sheath.
Figure 9:
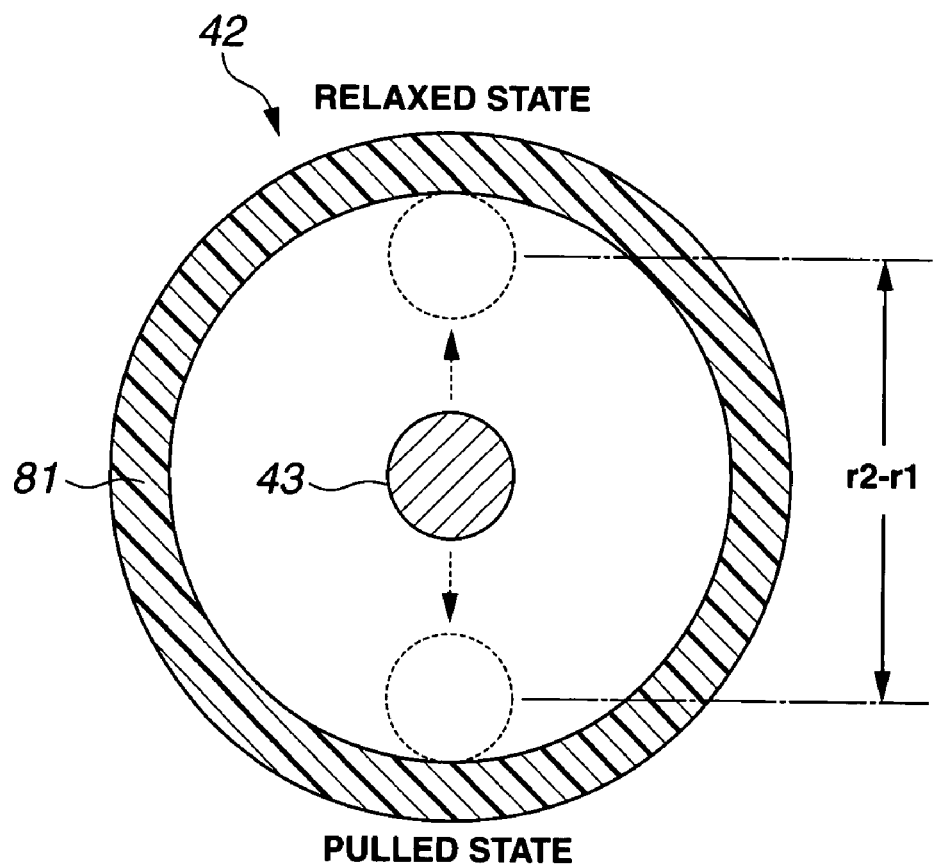
FIG. 9 is a section view along IX-IX line of FIG. 8 according to the second embodiment.
Figure 11:
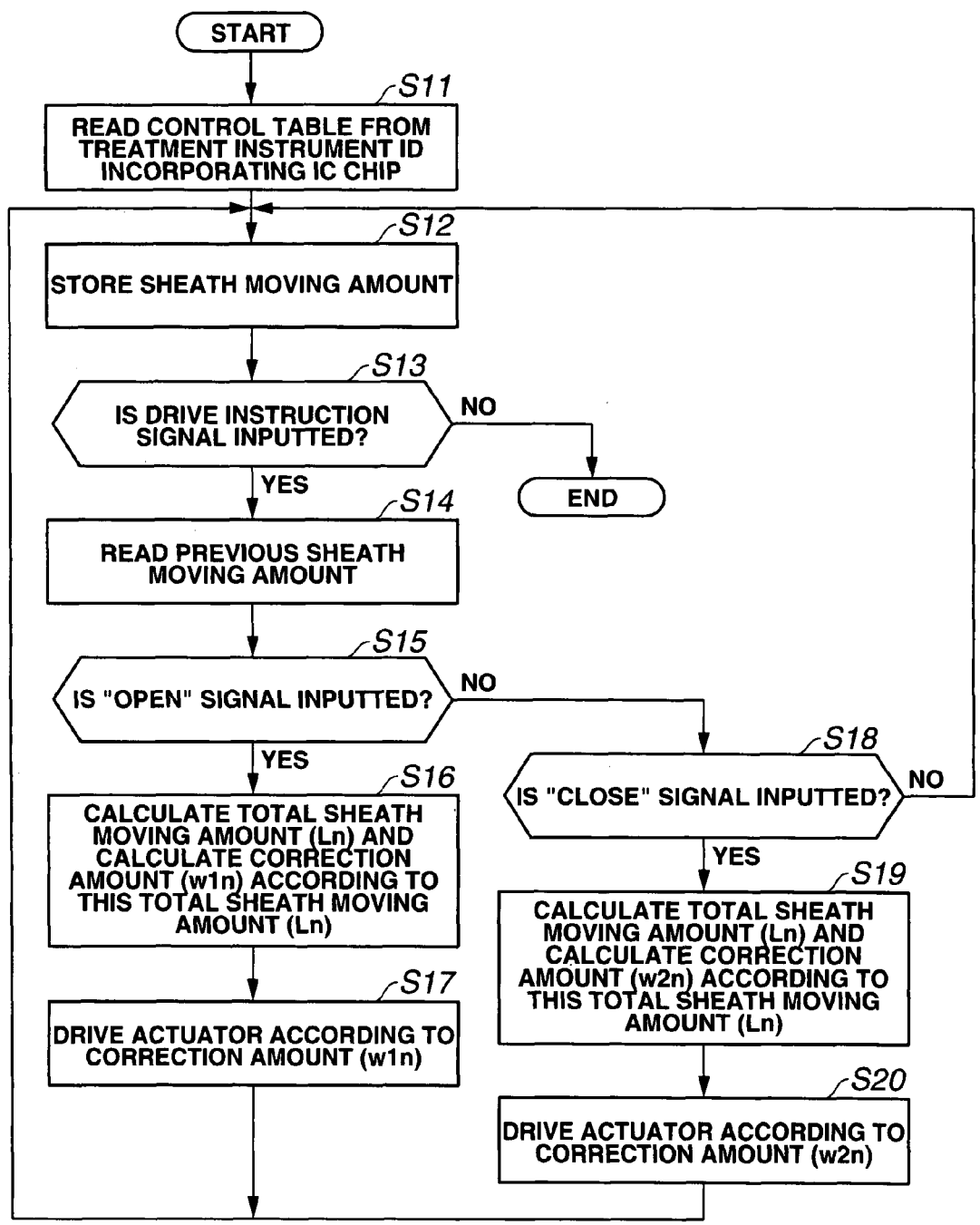
FIG. 11 is a flow chart of a control performed by the control device according to the second embodiment.

Note that FIGS. 8 to 11 relate to the second embodiment of the present invention, where FIG. 8 is a plan view showing configurations of the same two treatment instruments and showing states of a treatment portion due to characteristics of a sheath; FIG. 9 is a section view along IX-IX line of FIG. 8; FIG. 10 a view showing a control table of correction moving amounts of position of a slider for pulling and relaxing an operation wire, corresponding to moving amounts of the sheath, when opening/closing operation of the treatment portion is performed; and FIG. 11 is a flow chart of a control performed by the control device.

In the present embodiment, the sheath 42 of the treatment instrument 40 is a tube sheath type here, and only the control example of the control device 20 concerning opening/closing operation of the treatment portion 41 of the treatment instrument 40 is different, the other configurations being the same as in the first embodiment. Accordingly, only different parts are described using the same symbols for respective components.

As shown in FIG. 8, the treatment instrument 40 of the present embodiment exemplifies a conventionally available high-frequency snare. Since the high-frequency snare applies high frequency to the treatment portion 41 which is a loop-shaped metal snare through a metal operation wire 43, the sheath 42 has an insulation tubular body 81 formed by a non-metallic synthetic resin or the like (the treatment instrument of the present embodiment is hereinafter described as a high-frequency snare 40). The handle portion 44 is provided with a high-frequency cable connection portion not shown to be connected with a high-frequency cable that is electrically connected to the control device 20.

Because the sheath 42 is the insulation tubular body 81, the entire length of the high-frequency snare 40 does not expand or contract between looped state and generally straight state of the sheath 42, unlike the coil sheath type of the first embodiment.

However, with the high-frequency snare 40, an error occurs between looped state and generally straight state of the sheath 42, in the moving distance of the slider 46 as the treatment portion 41 is operated to move to advance or retreat, due to the relation between the inside diameter of the insulation tubular body 81 and the diameter of the operation wire 43.

As for the high-frequency snare 40, for example, when the treatment portion 41 is extended from a distal end aperture of the sheath 42 by a length Wn, in a generally straight state of the sheath 42, the moving distance of the slider 46 that pushes forward and relaxes the operation wire 43 is the same (the length Wn), as shown in FIG. 8.

On the other hand, as for the high-frequency snare 40, for example, when the treatment portion 41 is extended from a distal end aperture of the sheath 42 by the length Wn, in a looped state of the sheath 42, the moving distance of the slider 46 that pushes forward and relaxes the operation wire 43 has an error of a length w1n that occurs with respect to the moving distance Wn in the straight state, depending on the predetermined radius and the number of windings of the looped part of the sheath 42. An error in the moving distance also occurs when the slider 46 is moved rearward that is the opposite direction, to pull and draw the operation wire 43, in the looped state of the sheath 42.

In detail, the operation wire 43 that is freely inserted in the sheath 42, when pushed forward into a relaxed state, moves in a state in contact with an inner circumferential surface of the insulation tubular body 81 on an outer circumferential side of the sheath 42, in the loop of the sheath 42, as shown in FIG. 9. Meanwhile, the operation wire 43, when pulled rearward into a pulled state, moves in a state in contact with an inner circumferential surface of the insulation tubular body 81 on an inner circumferential side of the sheath 42, in the loop of the sheath 42.

For example, if the sheath 42 is looped in a single essentially true circle having a center O, the operation wire 43 when relaxed slides on a circumference of a radius r2 shown in FIG. 8, whereas the operation wire 43 when pulled slides on a circumference of a radius r1 shown in FIG. 8. Therefore, the operation wire 43 in this case has a length difference of $2\pi(r2-r1)$ to occur ($\pi$ being pi) in the distance to move to extend the treatment portion 41 with respect to, or house the same in the sheath 42, in the looped state of the sheath 42.

In other words, depending on the aperture diameter of the sheath 42, a difference occurs in the passage locus by the advancing/retreating movement of the operation wire 43. Note that, at part of the sheath 42 that is in a straight state, the operation wire 43 is supposed to pass through the generally center of the insulation tubular body 81.

Thus, when the high-frequency snare 40 including the sheath 42 of the tube sheath type is used in the endoscope system 1, the control device 20 performs control to correct the error that occurs in the opening/closing operation of the treatment portion 41 by advancing/retreating the operation wire 43, in line with the winding state of the sheath 42 housed in the case body 60. Note that the phenomenon of this error occurring, which here is mentioned concerning the tube sheath type, also occurs with the coil sheath type, of course.

The treatment instrument ID incorporating IC chip 49 incorporated in the handle portion 44 of the high-frequency snare 40 of the tube sheath type stores a control table in which correction moving amounts $w1_0$ to $w1n$ and $w2_0$ to $w2n$ of the operation wire 43 are set, which occur in opening/closing operation of the treatment portion 41 by pulling/relaxing the operation wire 43, with respect to moving amounts 0 to Ln of the sheath 42 that is fed to the treatment instrument channel 14a of the endoscope 10 from the initial state of being wound and housed in the case body 60, as shown in FIG. 10.

The endoscope system 1 of the present embodiment thus configured performs control to correct the position of the slider 46 of the high-frequency snare 40 by the control device 20, when the treatment portion 41 is operated to open/close by advancing or retreating the high-frequency snare 40 of the tube sheath type. In other words, the control device 20 performs control in line with the routine of the flow chart shown in FIG. 10, based on an inputted control table.

The information of this control table is read by the treatment instrument ID reading sensor 52a of the ring retaining portion 52 and then outputted to the control device 20, when the finger-hook ring 45 of the high-frequency snare 40 is installed to the ring retaining portion 52 of the electrical drive operating device 50 in a predetermined manner, as in the first embodiment.

Specifically, first, the endoscope system 1 is set to the state shown in FIG. 2. Then, to lead the high-frequency snare 40 into the treatment instrument channel 14a of the endoscope 10, the operator operates to incline forward the operation lever 34 of the controller 30. This causes the control device 20 to drive the electrical drive advancing/retreating device 70, as in the first embodiment. Further, the sheath 42 of the high-frequency snare 40 is fed by the pinching two rollers 71 into the treatment instrument channel 14a of the endoscope 10 via the coupling tube 78.

At this time, the control device 20 performs control based on the routine (step S) of the flow chart shown in FIG. 11, triggered by an advancing/retreating drive instruction signal from the operation lever 34 of the controller 30.

First, as shown in FIG. 11, the control device 20 reads the control table shown in FIG. 10 inputted by the treatment instrument ID reading sensor 52a and stored in the treatment instrument ID incorporating IC chip 49 (S11). Then, the control device 20 stores the total moving amount of the sheath 42 (S12). Note that the control device 20 calculates a moving amount of the sheath 42 from a detection value of the rotation detecting sensor 72 provided in the electrical drive advancing/retreating device 70. At the stage of the initial state, the sheath 42 is in a state of having a moving amount Ln wherein n=0 because the rotation detecting sensor 72 does not perform any detection.

Next, the control device 20 judges whether or not the advancing/retreating drive instruction signal is inputted from the operation lever 34 of the controller 30 (S13). At this time, if the advancing/retreating drive instruction signal is inputted, the control device 20 reads the total moving amount Ln (here, n=0) of the sheath 42 up until the last time, which is stored in step S12 (S14).

Next, the control device 20 judges whether or not there is inputted, from the operation lever 34 of the controller 30, an opening/closing drive instruction signal for "open" state for moving forward the slider 46 of the high-frequency snare 40 to advance the treatment portion 41 (S15).

At this time, if the opening/closing drive instruction signal for "open" is inputted, the control device 20 adds a moving amount Ln of the sheath 42 for this time detected by the rotation detecting sensor 72 and a sheath moving amount Ln of the previous time read in step S14, to calculate the total moving amount Ln of the sheath 42. Further, from the calculated total moving amount Ln and the control table shown in FIG. 10 that was read in step S11, the control device 20 calculates a correction moving amount w1n of the operation wire 43 to be pulled/relaxed by the slider 46, which corresponds to the total moving amount Ln (S16).

Then, in a manner corresponding to a moving amount obtained by adding a moving amount inputted from the controller 30 with the calculated correction moving amount w1n, the control device 20 drives the holding box 53 serving as an actuator, to move the slider 46 in a predetermined direction, which here is a forward direction (S17). Thereafter, the control device 20 returns to step S12 again.

If the opening/closing drive instruction signal for "open" is not inputted in step S15, the control device 20 judges whether or not there is inputted, from the operation lever 34 of the controller 30, an opening/closing drive instruction signal for the "close" state for moving rearward the slider 46 of the high-frequency snare 40 to retreat the treatment portion 41 (S18).

If at this time the opening/closing drive instruction signal for "close" is inputted, the control device 20 adds a moving amount Ln of the sheath 42 for this time detected by the rotation detecting sensor 72 and the sheath moving amount Ln for the previous time read in step S14, to calculate a total moving amount Ln of the sheath 42. Further, from the calculated total moving amount Ln and the control table shown in FIG. 10 that was read in step S11, the control device 20 calculates a correction moving amount w2n of the operation wire 43 for pulling/relaxing by the slider 46, which corresponds to the total moving amount Ln (S19).

Then, in a manner corresponding to a moving amount obtained by adding a moving amount inputted from the controller 30 with the calculated correction moving amount w2n, the control device 20 drives the holding box 53 serving as an actuator, to move the slider 46 in a predetermined direction, which here is a rearward direction (S20). Thereafter, the control device 20 returns to step S12 again.

If the opening/closing drive instruction signal for "close" is not inputted in step S18, the control device 20 returns to step S12 again.

In other words, the control device 20 repeats the routines of these steps S12 to S20. In step S13, if the advancing/retreating drive instruction signal is not inputted from the operation lever 34 of the controller 30, the control device 20 finishes the control flow chart of FIG. 11. That is, in this state, where the operator is not operating the operation lever 34 of the controller 30, the advancing/retreating movement of the sheath 42 of the high-frequency snare 40 is stopped, and the opening/closing operation of the treatment portion 41 of the high-frequency snare 40 is stopped.

As described above, when using a treatment instrument such as the high-frequency snare 40 here, including the sheath 42 of the tube sheath type, the endoscope system 1 of the present embodiment performs control to correct the error in the moving amount of the slider 46 connected to the operation wire 43 which occurs when pulling and relaxing the sheath 42, depending on the feeding amount of the sheath 42 wound and housed in the case body 60.

By this, the treatment portion 41 is led out from and into the distal end aperture of the sheath 42 in line here with a predetermined instruction of the controller 30, regardless of the feeding amount or extension amount of the sheath 42, that is, the housing amount into the case body 60. As a result, the opening/closing operation of the treatment portion 41 can be kept constant in line here with the predetermined rightward/leftward inclining operation of the operation lever 34 of the controller 30, thus allowing the endoscope system 1 of the present embodiment to prevent giving the operator as a user a sense of incongruity concerning the opening/closing operation of the treatment portion 41.

As a result of the foregoing, the endoscope system 1 of the present invention has a highly improved operability of reading the treatment instrument information from the treatment instrument 40 to be used, and automatically variably controlling the position and the moving operation of the slider 46 that operates the treatment portion 41, according to the types of the various treatment instruments 40 and configurations of the various sheaths 42. Note that the endoscope system 1 may perform control combining the above-mentioned exemplary control performed by the control device 20 of the first embodiment and the exemplary control performed by the control device 20 of the second embodiment.

The above-described invention is not limited to each of the embodiments, but can be implemented in other various modifications in practical stage without departing from the spirit of the invention. Moreover, each of the embodiments contains various stages of the invention, and various inventions can be extracted from appropriate combinations of the disclosed multiple constituent features.

For example, when an effect described as an effect of the invention is obtained for problems to be solved by the invention even if some constituent features are deleted from all the constituent features shown in each embodiment, the configuration deleted of the constituent features can be extracted as an invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A medical device for maintaining a state of a treatment portion of a treatment instrument, the medical device comprising:
    the treatment instrument including,
        the treatment portion which is used extended from a distal end of an endoscope insertion portion having a treatment instrument channel,
        an operation portion for operation of advancing/retreating an operation wire coupled to the treatment portion, and
        a treatment instrument insertion portion in which the operation wire is advanceably/retreatably inserted, the treatment instrument insertion portion having a predetermined flexibility and inserted into the treatment instrument channel;
    a detecting portion for detecting advancing/retreating moving amount of the treatment instrument insertion portion;
    a treatment portion operating device to which the operation portion is installed, the treatment portion operating device advancing/retreating the operation wire to operate the treatment portion;
    an operation instructing portion for instructing operation of the treatment portion;
    a case body for winding and housing the treatment instrument insertion portion; and
    a control device configured:
        to calculate a correction moving amount of the operation wire to maintain the treatment portion of the treatment instrument insertion portion in a closed state during insertion of the treatment portion into the treatment instrument channel, based on the advancing/retreating moving amount of the treatment instrument insertion portion wound and housed in the case body detected by the detecting portion, and
        to output a drive control signal to the treatment portion operating device so as to move the operation wire according to the calculated correction moving amount to maintain the treatment portion in a closed state.

2. The medical device according to claim 1, comprising a treatment instrument advancing/retreating device for inserting and advancing/retreating the treatment instrument insertion portion in the treatment instrument channel,
wherein the detecting portion detects the advancing/retreating moving amount of the treatment instrument insertion portion with respect to the case body, by a driving state of the treatment instrument advancing/retreating device.

3. The medical device according to claim 2, wherein
the treatment instrument is provided with a treatment instrument information identification portion storing at least the treatment instrument insertion portion information of the treatment instrument,
the medical device includes reading portion for reading the treatment instrument insertion portion information from the treatment instrument identification portion and outputting the treatment instrument insertion portion information to the control device, and
the control device calculates the moving amount obtained by correcting the advancing/retreating amount of the operation wire according to type of the treatment instrument insertion portion, based on the treatment instrument insertion portion information from the treatment instrument information identification portion, depending on a state of the treatment instrument insertion portion.

4. The medical device according to claim 3, wherein the treatment instrument identification portion is provided to an operation portion of the treatment instrument, and the reading portion is provided to the treatment portion operating device.

5. The medical device according to claim 2, wherein the treatment instrument advancing/retreating device includes rollers for moving to advance/retreat the treatment instrument insertion portion and a driving source for rotationally driving the rollers.

6. The medical device according to claim 5, wherein the detecting portion is a rotation detecting sensor which detects advancing/retreating moving amount of the treatment instrument insertion portion based on the number of rotations of the rollers.

7. The medical device according to claim 1, wherein
the treatment instrument is provided with a treatment instrument information identification portion storing at least the treatment instrument insertion portion information of the treatment instrument,
the medical device includes a reading portion for reading the treatment instrument insertion portion information from the treatment instrument identification portion and outputting the treatment instrument insertion portion information to the control device, and
the control device calculates the moving amount obtained by correcting the advancing/retreating amount of the operation wire according to type of the treatment instrument insertion portion, from the treatment instrument insertion portion information from the treatment instrument information identification portion, depending on a state of the treatment instrument insertion portion.

8. The medical device according to claim 7, wherein the treatment instrument identification portion is provided to an operation portion of the treatment instrument, and the reading portion is provided to the treatment portion operating device.

9. The medical device according to claim 1, wherein
the treatment instrument includes an opening/closing member at the treatment portion, and
the control device drives the treatment portion operating device to correct an opening/closing amount of the opening/closing member, according to change in the state of the treatment instrument insertion portion.

10. The medical device according to claim 9, wherein the control device drives the treatment portion operating device such that the treatment portion performs a constant opening/closing operation, by calculating a moving amount of the operation wire according to an opening/closing instruction for the treatment portion by the operation instructing portion, and a correction moving amount of the operation wire according to change in the state of the treatment instrument insertion portion.

11. A medical device for maintaining a state of a treatment portion of a treatment instrument, the medical device comprising:
an endoscope including an endoscope insertion portion having a treatment instrument channel;
the treatment instrument including:
the treatment portion which is used extended from a distal end of the endoscope insertion portion,
an operation portion for operation of advancing/retreating an operation wire coupled to the treatment portion, and
a treatment instrument insertion portion in which the operation wire is advanceably/retreatably inserted, the treatment instrument insertion portion having a predetermined flexibility and inserted into the treatment instrument channel;
a detecting portion for detecting advancing/retreating moving amount of the treatment instrument insertion portion;
a treatment portion operating device to which the operation portion is installed, the treatment portion operating device advancing/retreating the operation wire to operate the treatment portion;
an operation instructing portion for instructing operation of the treatment portion;
a case body for winding and housing the treatment instrument insertion portion; and
a control device configured:
to calculate a correction moving amount of the operation wire to maintain the treatment portion of the treatment instrument insertion portion in a closed state during insertion of the treatment portion into the treatment instrument channel, based on the advancing/retreating moving amount of the treatment insertion portion wound and housed in the case body detected by the detecting portion, and
to output a drive control signal to the treatment portion operating device so as to move the operation wire according to the calculated correction moving amount to maintain the treatment portion in a closed state.

* * * * *